(12) United States Patent
Alsop

(10) Patent No.: US 7,369,888 B2
(45) Date of Patent: *May 6, 2008

(54) MULTI-SLICE CEREBRAL BLOOD FLOW IMAGING WITH CONTINUOUS ARTERIAL SPIN LABELING MRI

(75) Inventor: David C. Alsop, Newton, MA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 48 days.

This patent is subject to a terminal disclaimer.

(21) Appl. No.: 11/198,581

(22) Filed: Aug. 5, 2005

(65) Prior Publication Data

US 2005/0277828 A1 Dec. 15, 2005

Related U.S. Application Data

(63) Continuation of application No. 09/673,049, filed as application No. PCT/US99/08087 on Apr. 13, 1999, now Pat. No. 6,980,845.

(60) Provisional application No. 60/081,506, filed on Apr. 13, 1998.

(51) Int. Cl.
*A61B 5/055* (2006.01)

(52) U.S. Cl. .................................... 600/419

(58) Field of Classification Search ............... 600/410, 600/419; 324/306
See application file for complete search history.

(56) References Cited

U.S. PATENT DOCUMENTS

| | | | |
|---|---|---|---|
| 4,777,957 A | 10/1988 | Wehrli et al. | 128/653 |
| 5,320,099 A | 6/1994 | Roberts et al. | 128/653.3 |
| 5,408,180 A | 4/1995 | Mistretta et al. | 324/306 |
| 5,417,214 A | 5/1995 | Roberts et al. | 128/653.3 |
| 5,792,054 A | 8/1998 | Kouwenhoven et al. | 600/410 |
| 6,493,569 B2 | 12/2002 | Foo et al. | 600/410 |
| 6,717,405 B2 | 4/2004 | Alsop | 324/306 |
| 2003/0193334 A1 | 10/2003 | Alsop | 324/306 |

FOREIGN PATENT DOCUMENTS

EP 0 582 967 A1 2/1994

OTHER PUBLICATIONS

Dixon, W.T., et al., "Projection angiograms of blood labeled by adiabatic fast passage," *Magnetic Resonance in Medicine*, 1986, 3, 454-462.
Communication dated Jun. 25, 2002 (EP 99 91 8519).

*Primary Examiner*—Ruth S. Smith
(74) *Attorney, Agent, or Firm*—Woodcock Washburn LLP

(57) ABSTRACT

This invention is a method for multi-slice CBF imaging using continuous arterial spin labeling (CASL) with an amplitude modulated control which is both highly effective at controlling for off resonance effects, and efficient at doubly inverting inflow spins, thus retaining the signal advantages of CASL versus pulsed ASL techniques.

4 Claims, 7 Drawing Sheets

Labeling Period

Delay    Imaging

MULTI-SLICE CEREBRAL BLOOD FLOW IMAGING WITH CONTINUOUS ARTERIAL SPIN LABELING MRI

CROSS-REFERENCE TO RELATED APPLICATIONS

This application is a continuation of U.S. application Ser. No. 09/673,049 filed Oct. 10, 2000, now U.S. Pat. No. 6,980,845, which is the national phase of PCT application No. PCT/US599/08087 filed Apr. 13, 1999, which claims benefit of U.S. Provisional application Ser. No. 60/081,506 filed Apr. 13, 1998, the contents of which are hereby incorporated by reference.

GOVERNMENT SUPPORT

This invention was supported by funds from the U.S. Government (National Institutes of Health grants NS01668, P30-MH93880, and P50-NS08803) and the U.S. Government may therefore have certain rights in the invention.

BACKGROUND OF THE INVENTION

1. Field of the Invention

The present invention relates to a technique for imaging regional cerebral blood flow (CBF) noninvasively using MRI with radio frequency arterial spin labeling and, more particularly, to a labeling technique which permits extension of this technique to a multi-slice examination.

2. Description of the Prior Art

The measurement of regional cerebral blood flow (CBF) is known to provide useful information both about cerebrovascular sufficiency and about regional brain metabolism because resting CBF and tissue metabolism are often strongly coupled. CBF imaging with Single Photon Computed Tomography (SPECT), Positron Emission Tomography (PET) and Xenon enhanced CT have been used to evaluate a multitude of cerebral disorders including stroke, dementia, epilepsy, trauma and neoplasms. PET imaging of CBF has also been an important tool for mapping task induced brain activity in normal and pathologic states. However, for most central nervous system disorders, Magnetic Resonance Imaging(MRI) provides the greatest sensitivity to structural abnormalities. A robust MRI based method for clinical imaging of CBF would allow both an anatomical and a functional assessment within the same examination. In addition to providing direct structure-function correlation, the higher spatial resolution of MRI as compared to nuclear medicine methods will lead to better image quality.

MRI of CBF can be performed either with intravascular contrast agents or by Arterial Spin Labeling (ASL). As known to those skilled in the art, instead of using an exogenous tracer, ASL electromagnetically labels water proton spins in the feeding arteries before they flow into the tissue. ASL is attractive since it can reduce the risk, complexity, and cost of a study. It is also more readily quantified and repeated than contrast agent methods.

Arterial Spin Labeling (ASL) techniques can be crudely divided into pulsed inversion techniques, such as EPISTAR, FAIR and other variants, and techniques which employ continuous arterial spin labeling (CASL). CASL produces more than twice the signal of pulsed techniques. Unfortunately, with both methods, multi-slice imaging is complicated by effects of the electromagnetic labeling on the image intensity, as well as the relatively long time required for blood to flow from the arteries into the thick slab of tissue to be imaged.

The ASL approach to MRI of CBF offers the potential for completely non-invasive, quantitative imaging of an important physiologic and diagnostic quantity; however, practical implementations of ASL in humans have typically suffered from systematic errors and artifacts which can only be corrected one slice at a time and which have thus limited its applicability. Recently, the use of fast imaging methods and an increased understanding of the factors affecting quantification of CBF have led to the acquisition of single-slice CBF images of good quality such that clinical and research applications can be explored. Unfortunately, most applications require greater slice coverage but the serial acquisition of many slices can be prohibitively time consuming. However, improved Radio Frequency (RF) pulse shapes and sequence design has made multi-slice pulsed ASL techniques feasible and multi-slice perfusion imaging more practical for diagnosis.

Accordingly, a method is desired which makes possible multi-slice imaging of CBF with good signal-to-noise ratio and arbitrary angles between imaging and labeling planes. The present invention is designed to meet this need in the art.

SUMMARY OF THE INVENTION

The present invention relates to a method for generating two sets of images which are identical except for the effects of blood flowing into the imaged slices. Subtraction of the two images can provide images of blood flowing in large vessels, sometimes referred to as angiograms, or perfusion, sometimes referred to as tissue specific blood flow, depending upon the timing of the imaging sequence. In particular, the present invention relates to the use of amplitude modulated RF irradiation prior to the acquisition of one set of images, hereafter referred to as the control images, and the use of unmodulated RF irradiation prior to the acquisition of the second set of images, hereafter referred to as the labeled images. It is known in the prior art that constant RF irradiation, in combination with a magnetic field gradient, can change the MR signal of flowing blood from positive to negative. The present invention employs the amplitude modulated RF irradiation prior to the control image acquisition to mimic all the blood flow unrelated effects of the constant RF irradiation while leaving the blood signal positive. While prior art techniques for the control image were only effective in a single thin slice at a particular angular orientation or required a second RF coil, the amplitude modulated control approach of the invention is effective for any number, orientation, and thickness of slices.

In particular, the invention relates to a method for imaging blood flow into a sample such as a tissue sample or a large blood vessel. A preferred embodiment of the inventive method comprises the steps of:

perturbing arterial spins of blood flowing into the sample by applying a constant RF irradiation together with a magnetic field gradient;

acquiring a first image of the sample;

applying amplitude modulated RF irradiation with a magnetic field gradient which, together, mimic the effects of constant RF radiation unrelated to blood flow;

acquiring a second image of the sample; and generating a difference signal based on the first image and the second image that represents a blood flow image of blood flowing into the sample.

In a preferred embodiment of the invention, the first image is acquired after a delay period by detecting a magnetic resonance signal reflected off of the sample. The delay period is set either to allow the blood having the perturbed spins to flow into the tissue before the images are captured (i.e., to capture a perfusion image), or to ensure that the images are captured while the blood is still in the blood vessel (i.e., to capture a large vessel blood flow image). The second image is acquired in a similar fashion shortly after the amplitude modulated RF irradiation is applied. The analog magnetic resonance signals are preferably digitized and processed to measure blood flow via known techniques.

BRIEF DESCRIPTION OF THE DRAWINGS

The foregoing and other novel features and advantages of the invention will become more apparent and more readily appreciated by those skilled in the art after consideration of the following description in conjunction with the associated drawings, of which.

DETAILED DESCRIPTION OF THE PRESENTLY PREFERRED EMBODIMENTS

A preferred embodiment of the invention will now be described in detail with reference to FIGS. 1-7. Those skilled in the art will appreciate that the description given herein with respect to those figures is for exemplary purposes only and is not intended in any way to limit the scope of the invention. All questions regarding the scope of the invention may be resolved by referring to the appended claims.

MATERIALS AND METHODS

Amplitude Modulated Control

Continuous application of off resonance RF power causes saturation of image intensity due to the finite width of the water line and the transfer of saturated magnetization from water molecules adjacent to macromolecules, which have much broader lines. The off-resonance inversion power applied in CASL usually causes such saturation and its presence complicates CBF imaging since the off-resonance effects may be large compared to the effects of blood flow. An approach to eliminating this saturation is the use of a second small RF coil for labeling that is far enough from the imaged slice that the off-resonance power is negligible. This method has been previously used successfully to obtain multi-slice CBF images in a rat brain but it requires special RF hardware and a favorable geometry for the labeling which limits its applicability. The alternative is to control for the saturation. Since ASL CBF imaging relies on the subtraction of the labeled image from a reference image obtained without labeling, achieving equal off-resonance saturation in the reference image will control for the saturation effect.

Figure 1A:
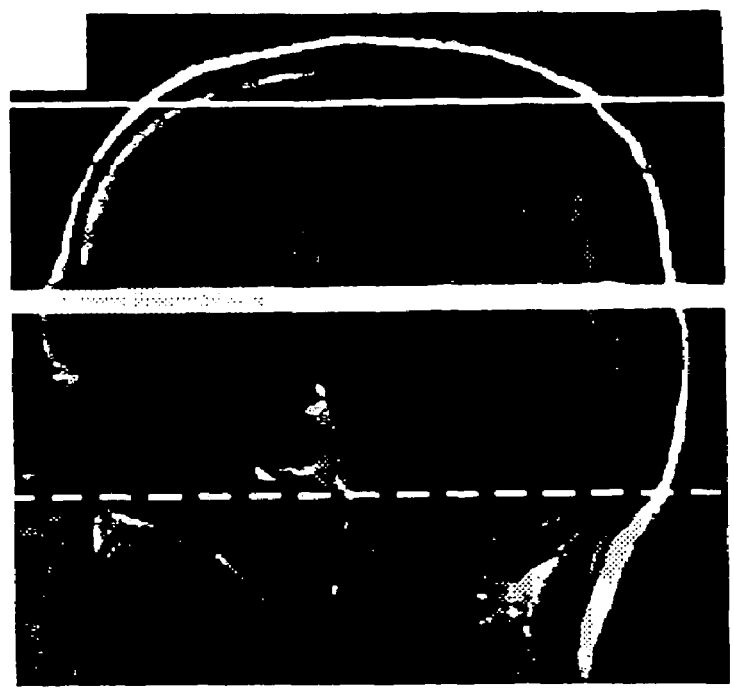
FIG. 1A illustrates a single slice experiment in which the control labeled images are acquired with labeling applied at an equal distance distal to the slice (solid line) to compensate for the spatially dependent off resonance effects.

FIG. 1 illustrates control methods for CASL imaging of CBF. RF irradiation used to label inflowing blood as it crosses the labeling plane (dashed line) also causes direct effects on image intensity that vary with distance from the labeling plane. The established method of controlling for off resonance saturation with a single RF coil was to apply an inversion distal to the slice during the control image, as illustrated in FIG. 1A. FIG. 1A illustrates a single slice experiment in which the control labeled images are acquired with labeling applied at an equal distance distal to the slice (solid line) to compensate for the spatially dependent off resonance effects. If there are no significant background magnetic field gradients in the sample (e.g., the tissue or blood vessel), the off-resonance saturation is symmetric in frequency, and the labeling and control inversion are parallel to and equidistant to the image slice, then the control image will experience equal off-resonance saturation. However, the requirement that the labeling and control inversion planes be equidistant to and parallel to the image.slice restricts the geometry of ASL CBF images and is not readily extended to a multi-slice examination. To overcome these limitations, an alternative control irradiation which mimics the frequency dependent off-resonance effects of the labeling irradiation is required.

Figure 1B:
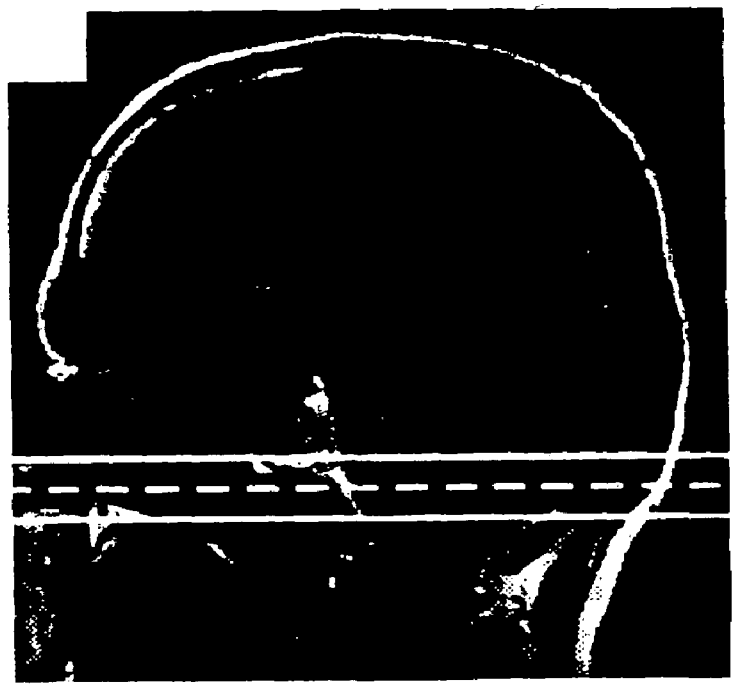
FIG. 1B illustrates the amplitude modulated irradiation technique of the invention whereby two inversion planes are created close to the original labeling plane.

Thus, in the method of the invention, applying an amplitude modulated form of the labeling RF irradiation for the control was evaluated. In particular, it was observed that when a constant RF irradiation at a fixed frequency, $f_o$, is multiplied by a sine wave at frequency $f_1$, the signal produced is mathematically identical to continuous irradiation at two different frequencies, $f_0+f_1$ and $f_0-f_1$. If applied in the presence of a magnetic field gradient, each would separately perturb, such as by adiabatic inversion, inflowing arterial spins. When performed simultaneously, the combined effect is complicated because the equations governing spin evolution are not linear in the applied RF. However, the nature of resonance. suggests that the effect of the first inversion on spins located near the second inversion plane should be small as long as the frequency spacing between the planes is large. In this case, the spins will be inverted twice after flowing through the two inversion planes, as illustrated in FIG. 1B. In FIG. 1B, the amplitude modulated irradiation creates two inversion planes (solid lines) close to the original labeling plane. Ideally, the inflowing spins are inverted twice as they flow through the planes producing no net effect on arterial labeling while the spatially dependent off resonance effects of the RF irradiation are precisely reproduced. Double inversion produces no net effect, so spins would not be labeled by the amplitude modulated control. Because the average power and center frequency of the amplitude modulated control are identical to the labeling RF irradiation, the off-resonance effects of the control are nearly identical to those of the labeling.

The performance of amplitude modulation of the RF irradiation as a control will depend on how perfectly the spins are doubly inverted, and on how well the off-resonance saturation of the labeling irradiation is matched. If the spins are partially labeled by the amplitude modulated control, then the difference between the labeled and control images will decrease. This can be thought of as a loss of efficiency for labeling of blood flow. If the control does not perfectly match the off-resonance saturation of the labeling, then a difference between the images will occur even in the absence of blood flow. This would represent a systematic error in the blood flow measurement. Both of these properties of the control were assessed experimentally as described below.

Imaging

All studies using the techniques of the invention were performed on a 1.5 Tesla GE SIGNA clinical scanner equipped with a prototype gradient system for echoplanar imaging. Gradient echo echoplanar images were obtained using a field of view of 24 cm along the frequency encoding direction and 15 cm for the phase direction and an acquisition matrix of 64×40. An acquisition bandwidth of ±62.5 kHz allowed an effective TE of 22 ms and an image acquisition time of 45 ms. Multi-slice image acquisition was performed without pausing between slices so that 8 slices could be acquired in less than 400 ms. Slice thickness ranged between 6 and 10 mm and interslice gaps of 2 mm between slices were used to minimize potential interference between slices.

Figure 2:
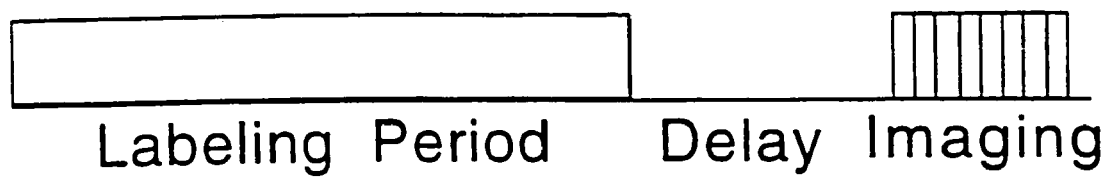
FIG. 2 illustrates a pulse sequence timing diagram for the entire sequence used to amplitude modulate the RF pulse in accordance with the method of the invention.

Spin labeling was performed for single slice CBF imaging except for the amplitude modulated control and the acquisition of more than one slice. Specifically, a TR of 4s, temporal interleaving of labeled and control images, and a post-labeling delay were employed. The post-labeling delay reduced the sensitivity of the CBF image to the transit time from the labeling plane, attenuated the signal from intraluminal arterial spins, and decreased the off-resonance saturation of the image intensity by the labeling RF. The post-labeling delay also allows time for all of the labeled blood to enter the tissue before imaging so that saturation of labeled spins by the imaging excitation pulses need not be considered. The duration of the labeling irradiation was determined by the post-labeling delay, the imaging time and TR. For a post-labeling delay of 1.2s, the irradiation was applied for 2.3s. A pulse sequence timing diagram for the entire sequence is shown in FIG. 2. In.the timing diagram of FIG. 2, labeling RF signals and gradients are applied during the labeling period. Rapid gradient echo echoplanar imaging was used to acquire images from the 8 slices.

In addition to the CBF scan, multi-slice versions of the conventional echoplanar T1 mapping scans were performed. The T1 maps are necessary for quantification of the CBF images. Unlike in the single-slice implementation, it was necessary to leave the labeling gradient on during T1 mapping to accurately measure the T1 shortening effect of the off-resonance saturation. In all other ways the protocol was identical. The entire T1 mapping protocol required 3 minutes for all slices.

All raw echo amplitudes were saved and transferred to a workstation for reconstructing the images. A correction for image distortion and alternate k-space line errors was performed on each image using data acquired during a phase encoded reference scan. As known to those skilled in the art, the correction for distortion involves the measurement of magnetic field nonuniformity throughout the image. A side-effect of this correction is that image regions where insufficient MR signal is present to accurately measure the magnetic field are set to zero. The magnitude images were then averaged and the CBF weighted images were calculated by subtraction of labeled images from the control images. An algorithm to remove subtle motion artifacts from the images was performed on the individual images prior to averaging for more accurate evaluation of the performance of the control.

Phantom Studies

Prior to evaluation in human subjects, the sequence was tested and calibrated on a uniform phantom consisting of 2% agarose by weight in distilled $H_2O$. Such a phantom with significant magnetization transfer was necessary to fully test the control. The magnetization transfer properties of agarose are well studied but considerably different from most human tissues. Since it was desired that the control would be accurate across a wide range of tissue types, the agarose phantom was selected since it served as an extreme case.

The phantom consisted of a cylindrical plastic container, 10 cm in diameter and 20 cm long, filled with the gelatinous mixture. The phantom was placed in the standard head coil of the scanner with the axis parallel to the axis of the magnet. Single-slice images employing the CBF labeling strategy were acquired in a plane perpendicular to the axis of the phantom. A labeling RF irradiation of 35 mG and a labeling gradient of 0.25 G/cm applied along the frequency direction of the image were used. Images were acquired with amplitude modulation frequencies of 125, 250 and 500 Hz. Off-resonance saturation was analyzed by averaging the images across the phase direction so that plots of off-resonance saturation as a function of frequency could be generated. During evaluation of the sequence, it was found that weak saturation of signal at the labeling plane occurred even when the RF amplitude was set to zero in software. This indicated that a small amount of RF was leaking past the modulator. The saturation could be eliminated by setting the RF amplitude to a small negative value corresponding to 2% of the RF amplitude used for labeling. A constant value of 2% of the signal amplitude was subtracted from the software values of all of the labeling related RF amplitudes to compensate for this carrier leakage. Failure to correct for this leakage would cause systematic error in the CBF measurement. Since the leakage is a subject independent phenomenon, it can be calibrated with phantom measurements and need never be measured in subjects.

Human Studies

Three different human studies were performed. In one study, the amplitude modulated control method was tested for systematic offset due to imperfect matching of the off-resonance saturation for label and control. Two subjects were scanned with a control modulation frequency of 250 Hz, an RF irradiation amplitude of 35 mG, a post-labeling delay of 1.2 s, and a 0.25 G/cm labeling gradient. Images from eight 8 mm thick slices were obtained from both subjects when the labeling was applied to the carotid and vertebral arteries at the ponto-medullary junction, to generate CBF images, and also when the labeling was applied distal to the imaging slice at the top of the brain, which should produce no flow-related signal in the absence of systematic error. One of the subjects was scanned in the axial plane while the other was scanned in the coronal plane to emphasize the flexibility of slice geometry made possible by the amplitude modulated control technique of the invention.

In a second study, the efficiency of the multi-slice CBF measurement was compared with the single slice method. CBF images were acquired in a single axial slice through the basal ganglia and thalamus in nine subjects. Images were acquired with both the single slice method, where the control is labeling distal to the slice, and the multi-slice method. All subjects were studied with a 0.25 G/cm labeling gradient, an RF irradiation amplitude of 35mG, a control modulation frequency of 250 Hz, a post-labeling delay of 1.2 s, and a labeling plane offset of between 4 and 8 cm from the slice. Between 15 and 45 difference images were averaged for each subject. In three of these subjects the single slice and multi-slice methods were also compared at RF amplitudes of 30 and 20 mG. In three other subjects, the methods were also compared with modulation frequencies of 62.5 Hz., 100 Hz, 125 Hz, 200 Hz and 500 Hz.

In the final human study, multi-slice CBF images and T1 maps were obtained with 250 Hz modulation and 35 mG RF amplitude in four subjects for quantitative analysis of CBF using prior art methods. The entire CBF imaging sequence required 9 minutes including T1 mapping and 45 averages of tagged and control images. The multi-slice labeling efficiency measured in the first study was used for quantification.

RESULTS

Phantom Study

Figure 3:
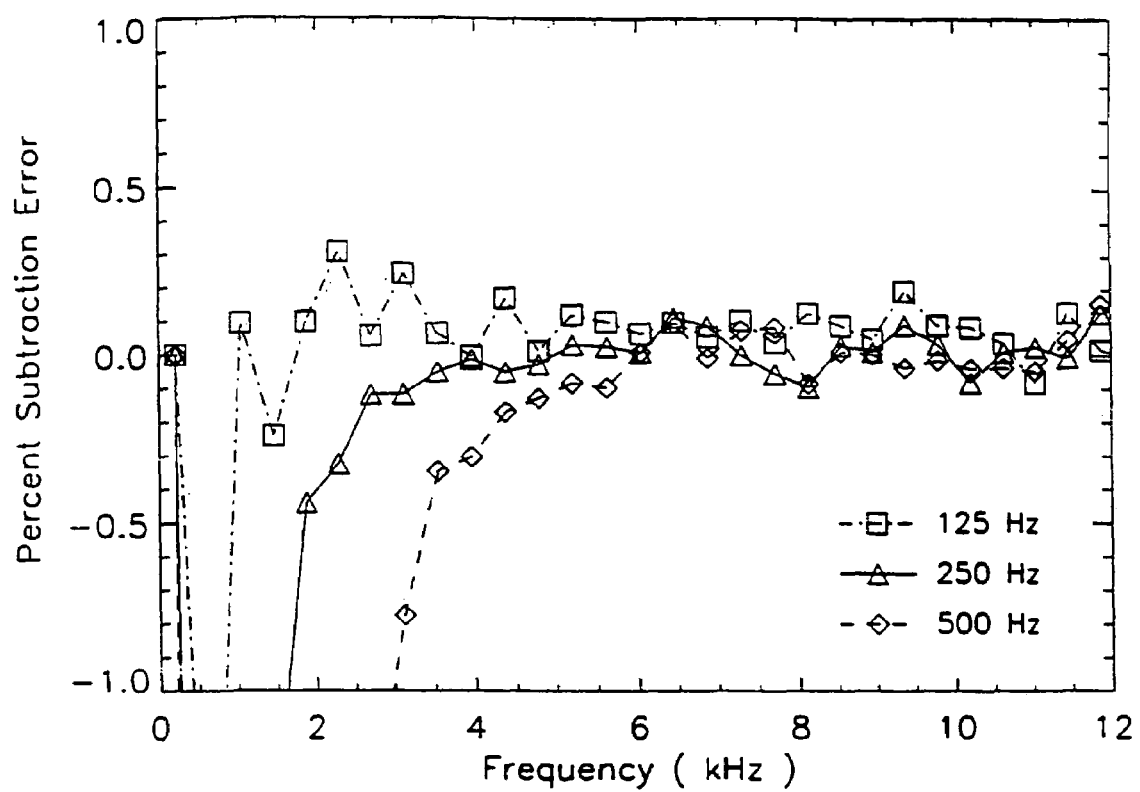
FIG. 3 illustrates the percent difference between labeling and control images in a phantom as a function of frequency.

Matching of frequency dependent off-resonance saturation effects between the labeling and amplitude modulated control was excellent at all three frequencies, as shown in FIG. 3, where the percent difference between labeling and control images in the phantom is shown as a function of frequency. Though both types of irradiation produced off-resonance saturation of greater than 15% of the unsaturated signal, the difference between the two was less than 0.1% except very close to the labeling plane. The frequency at which the difference between the labeled and control frequencies became significant was smaller for lower frequency amplitude modulation. This suggests that labeling can be performed closer to the most inferior region to be imaged when a slower amplitude modulation is used.

Human Studies

Figure 4:
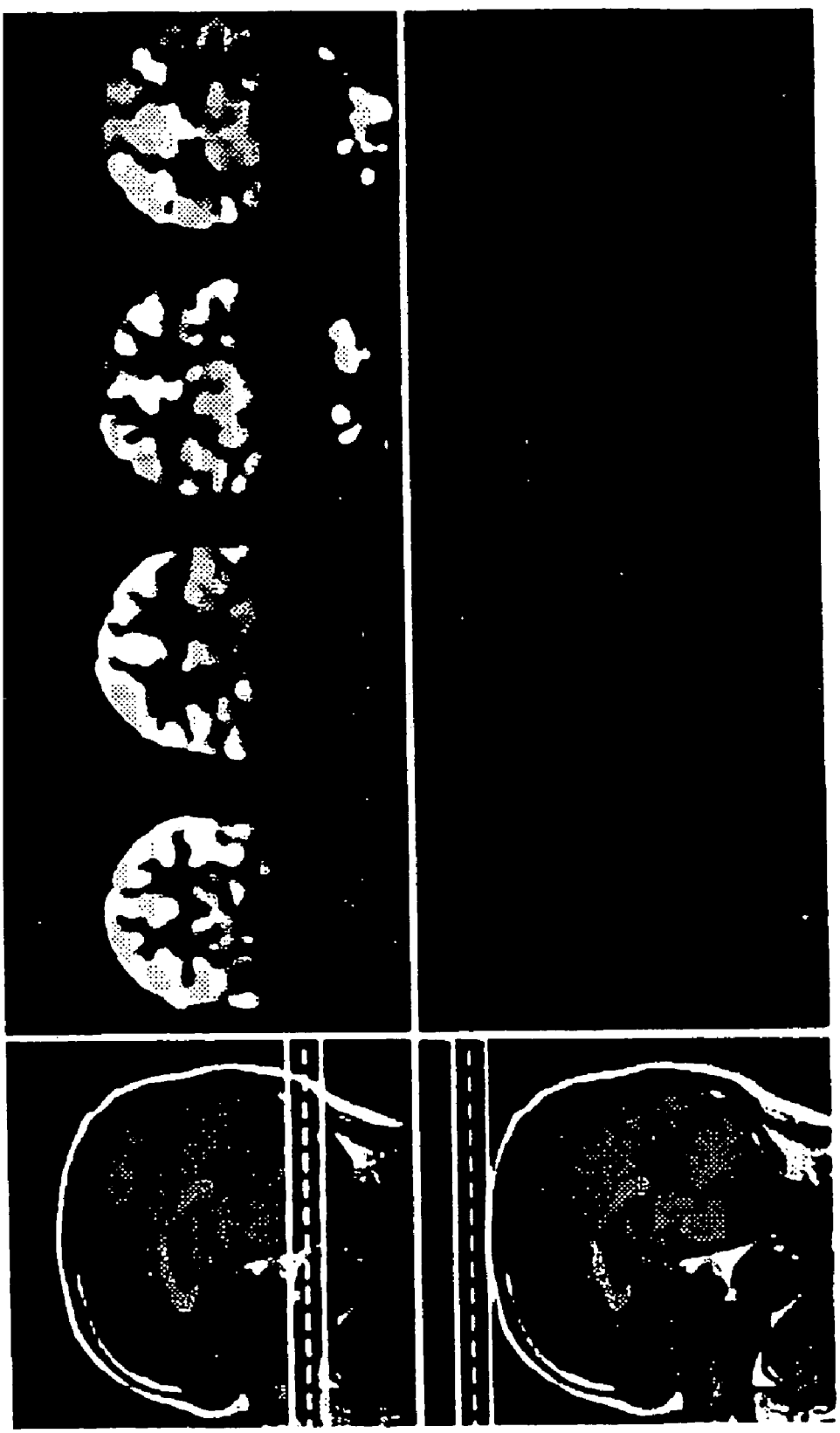
FIG. 4 illustrates coronal images acquired in a human study with the label and control respectively placed at the ponto-medullary junction and 2 cm above the brain as indicated on the sagittal T1 images on the left of the figure.

Excellent matching between the labeling and control off-resonance saturation in the phantom was also reproduced in the in vivo studies. FIG. 4 shows the coronal images acquired with label and control placed at the ponto-medullary junction and 2 cm above the brain as indicated on the sagittal T1 images on the left of the figure. Multi-slice difference images acquired with the proximal labeling (top right) demonstrate signal from CBF. Images acquired with the distal labeling (bottom right) show no significant signal. In other words, while the scans with the ponto-medullary junction label show strong perfusion signal in all distal regions of the brain, those with the label above the brain show no significant signal.

Figure 5:
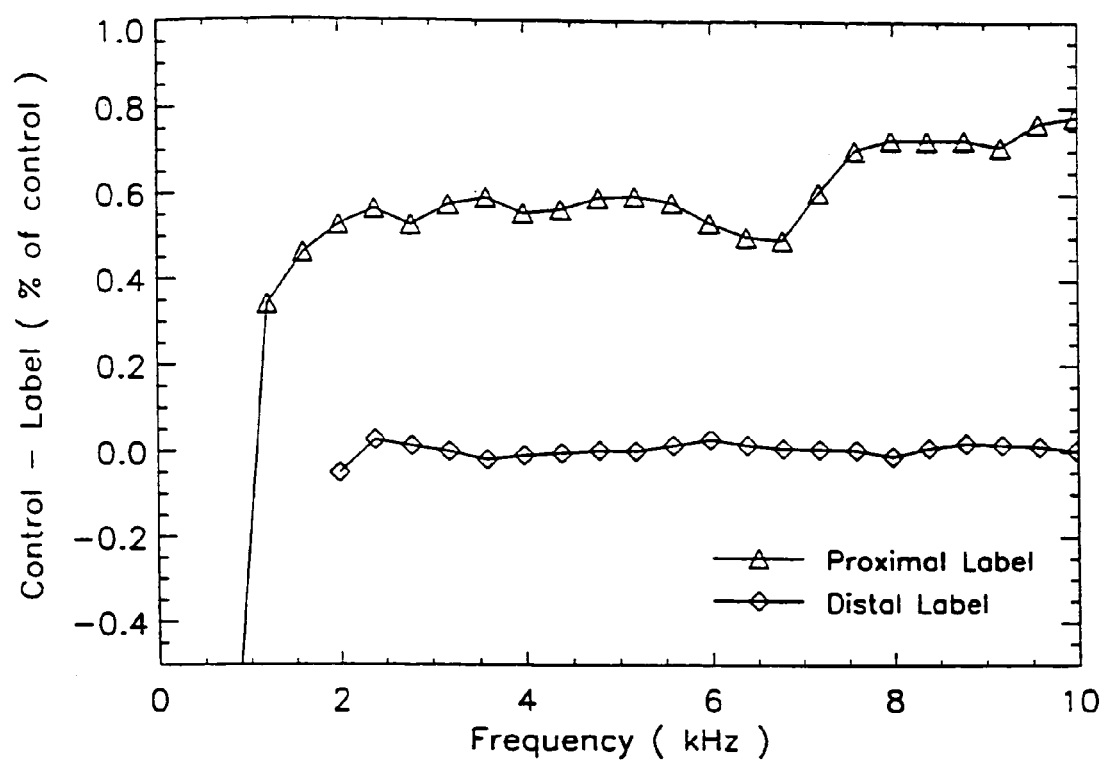
FIG. 5 illustrates a plot of the residual subtraction errors caused by imperfect matching of off-resonance saturation.

To further quantify residual subtraction errors caused by imperfect matching of off-resonance saturation, the image intensity was averaged across the slice and phase directions, similar to the phantom analysis, and the results were plotted in FIG. 5. In FIG. 5, the average difference signal was obtained by averaging the images of FIG. 3 across the anterior-posterior and right-left directions. Distance from the labeling plane was converted into frequency offset for plotting. As shown, proximal labeling at the ponto-medullary junction produced a small but very significant change in the image intensity due to CBF, while distal labeling above the brain produced no significant signal change consistent with negligible off-resonance errors for offset frequencies above 2 kHz.

While perfusion produces a signal change of under one percent in the proximal labeled scans, residual subtraction error for frequencies above 2 kHz as measured by the distal labeled scans is consistent with noise and is always less than 0.05 percent. The average of the subtraction signal across frequency from 2 to 10 kHz is less than 0.007 percent of the control image intensity. Since the CBF images were acquired in a plane perpendicular to the labeling plane, their uniformity is also a direct indicator of the accuracy of the control. Errors in subtraction are apparent in the perfusion signal of FIG. 5 very near the labeling plane at offset frequencies below 2 kHz. The subtraction error produces a shift to a negative signal consistent with the phantom results of FIG. 3.

Figure 6:
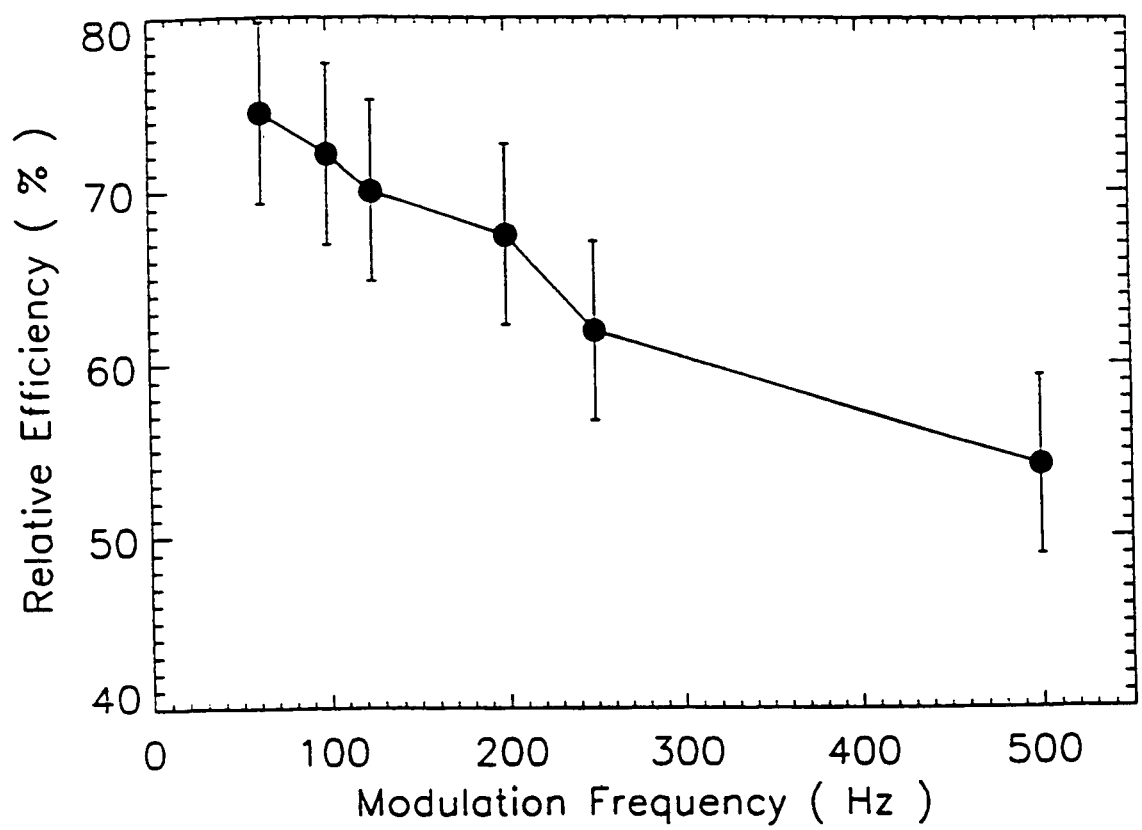
FIG. 6 illustrates the efficiency of spin labeling with amplitude modulated control as a function of modulation frequency relative to a single slice labeling.

The mean efficiency ratio of the multi-slice and single slice methods was 61.6% ±6.7% across the nine subjects when a modulation frequency of 250 Hz was used. This efficiency was found to drop rapidly when the amplitude of the RF was lowered; the efficiency at 30 mG was 58% and at 20 mG it was only 35%. As shown in FIG. 6, the efficiency of spin labeling with amplitude modulated control as a function of modulation frequency relative to a single slice labeling with 36 mG amplitude irradiation improved to 75% when the modulation frequency was lowered. This suggests that a modulation frequency of 62.5 Hz is more desirable than 250 Hz.

Figure 7:
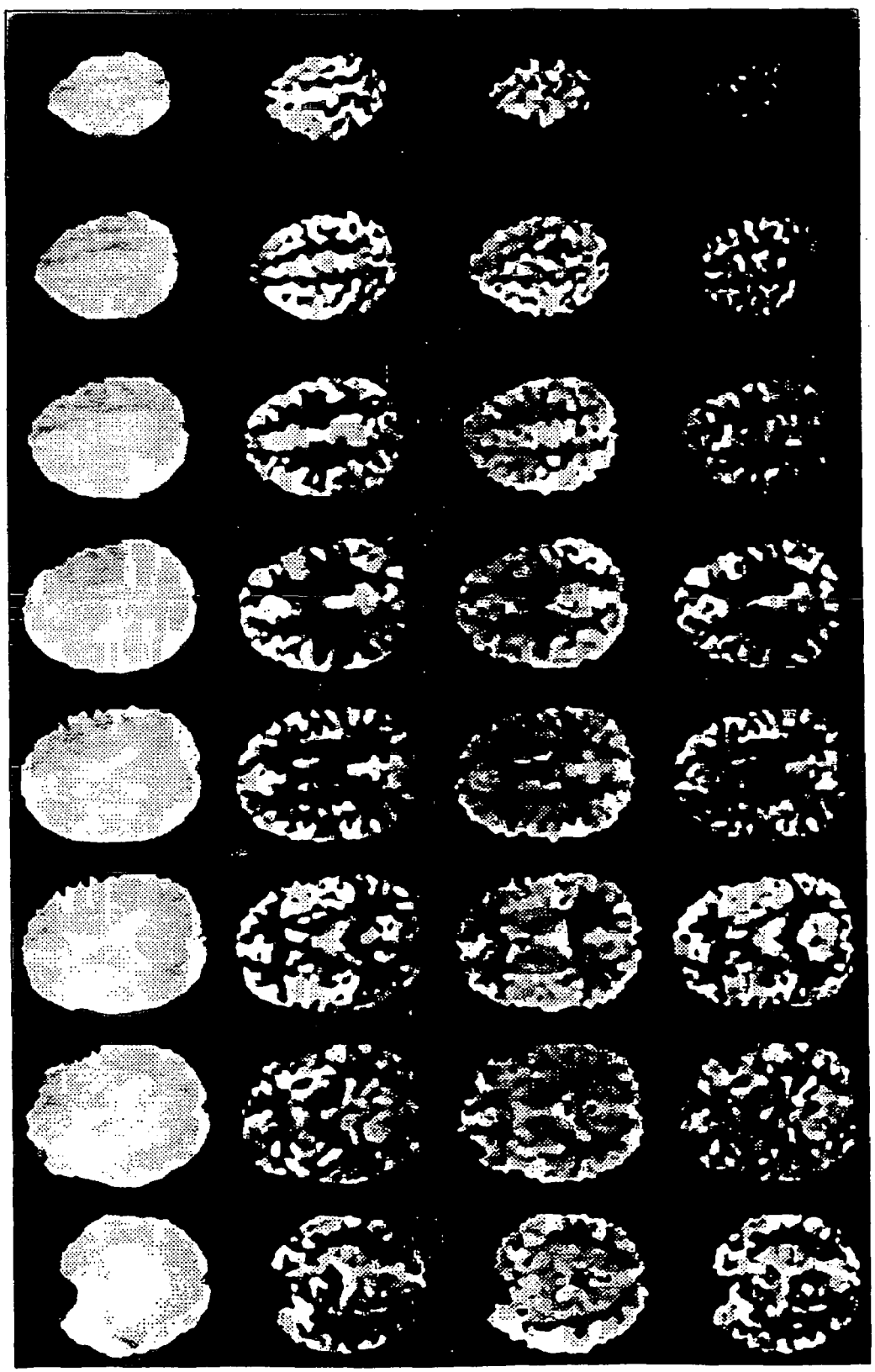
FIG. 7 illustrates echoplanar images from eight axial slices (top row) used to generate CBF sensitive images (second row) as well as acquired T1 maps (third row) used to generate quantitative images of CBF (bottom row).

Quantification of the CBF images was next performed using prior art methods for single slice imaging. The average of the labeled images was first subtracted from the average of the control images and then divided by the intensity of an image obtained in the absence of off resonance saturation. This ratio was then multiplied by a calibration factor which is a function of the calculated T1 images, the transit times to the tissue from the labeling plane, and the post-labeling delay for each slice. Because the transit time to the tissue was not measured, an assumed value of 1.5 s was employed for quantification. The long post-labeling delay minimized the sensitivity of the calibration factor to differences between the assumed and actual transit time. The images were corrected for inefficiency of labeling by dividing by an efficiency of 58.5%. This value was based on an efficiency of 95% for the single slice experiment and the measured ratio of multi-slice to single slice efficiency of 61.6%. Calculated images from one of the subjects are displayed in FIG. 7. In FIG. 7, echoplanar images from eight axial slices (top row) were used to generate CBF sensitive images (second row). Using the T1 maps also acquired (third row), quantitative images of CBF were generated (bottom row).

These images are not corrected for spatial variations in the blood-brain partition coefficient. Quantitative CBF values were derived by segmenting the tissue into gray and white matter based on the T1 maps and using a partition coefficient of 0.98 for gray matter and 0.82 for white matter. The measured CBF values are consistent with values for quantitative cerebral blood flow (ml 100 $g^{-1}$ min−1) obtained previously using single slice methods and with other measurements of CBF, as represented for four normal volunteers in Table 1.

TABLE 1

| Subject | Age | Sex | Gray Matter | White Matter | Mean |
|---|---|---|---|---|---|
| 1 | 24 | M | 70.5 | 27.1 | 53.7 |
| 2 | 25 | M | 71.4 | 28.5 | 54.8 |
| 3 | 32 | M | 61.7 | 32.5 | 50.4 |
| 4 | 21 | F | 85.9 | 49.7 | 71.9 |
| Mean | 25.5 ± 5 | | 72.4 ± 10 | 34.5 ± 10 | 57.7 ± 10 |

DISCUSSION

The invention relates to a method for multi-slice CBF imaging using CASL with an amplitude modulated control. This control strategy is both highly effective at controlling for off-resonance effects and efficient at doubly inverting inflowing spins, thus retaining the signal advantages of CASL versus pulsed ASL techniques. The method is readily implemented using standard hardware, is effective in both gray and white matter, and allows flexible selection of the imaging and labeling planes. Because the control method is applied at the same location as the labeling and gives equal effect across a wide range of frequencies, there should be no errors associated with static magnetic field inhomogeneity or asymmetry in the off-resonance spectrum. The labeling method is therefore highly desirable even for single-slice CBF imaging applications. This approach should also be applicable to blood flow measurements in organs other than the brain. Also, although the above studies were carried out in eight slices, the number of slices is limited only by the image acquisition time and T1 of blood and tissue.

The highest efficiency was measured for the lowest modulation frequency in the study, 62.5 Hz, which was contrary to the inventor's expectation that the two inversion planes would start to interfere as they became closer. The inventor has implemented numerical simulations of the control using methods similar to those published for single slice labeling. These simulations suggest that inefficiency results primarily from non-linear interactions between the two inversion planes rather than T1 decay between the two planes.

The use of gradient echo echoplanar imaging with a moderately long TE in this study caused signal loss in parts of the inferior frontal and temporal lobes because of non-uniform magnetic fields near bones and sinuses. Spin echo echoplanar was avoided because it would have increased the duration of image acquisition. Fractional k-space acquisition could have enabled much shorter effective TE gradient echo or spin echo echoplanar images with comparable or shorter acquisition times to the sequence. If necessary for image speed or quality, other imaging methods such as interleaved echoplanar or RARE might be employed as long as they do not unacceptably increase the motion artifact.

Spin labeled perfusion images clearly reflect CBF and its spatial and temporal variation but further work is required to test and validate the quantitative values obtained with the technique of the invention.

Those skilled in the art will appreciate that the extension of CASL CBF imaging to a multi-slice modality in accordance with the techniques of the invention overcomes a major obstacle to clinical applications. The techniques of the invention have already been successfully applied in patients with cerebrovascular disease. CBF measurements using this approach are also likely to provide a sensitive and quantitative measure of cerebrovascular reserve when carried out in conjunction with acetazolamide administration or $CO_2$ inhalation. Numerous other potential clinical applications can be envisioned, including the differential diagnosis of dementing disorders and cerebral neoplasms. In addition, quantitative CBF measurements have applications to clinical and basic neuroscience, for imaging regional CBF changes during sensorimotor or cognitive tasks or following pharmacological challenges, and for population-based studies of changes in regional CBF and metabolism.

Those skilled in the art will appreciate that numerous other modifications to the invention are possible within the scope of the invention. Accordingly, the scope of the invention is not intended to be limited to the preferred embodiments described above, but only by any appended claims.

What is claimed:

1. A method for generating a signal representative of a blood flow image, comprising the steps of:
   perturbing arterial spins of blood flowing into a sample by applying a constant RF irradiation together with a magnetic field gradient;
   waiting a transit delay period before acquiring a first image of the sample;
   acquiring the first image of the sample;
   applying amplitude modulated RF irradiation with a magnetic field gradient which, together, mimic the effects of constant RF radiation unrelated to blood flow;
   acquiring a second image of the sample;
   generating a difference signal based on the first image and the second image that represents a blood flow image of blood flowing into the sample; and
   determining a duration of the transit delay period so as to permit blood having perturbed arterial spins to flow into the sample, thus causing the blood flow image to be representative of perfusion.

2. A method for generating a signal representative of a blood flow image, comprising the steps of:
   perturbing arterial spins of blood flowing into a sample by applying a constant RF irradiation together with a magnetic field gradient;
   waiting a transit delay period before acquiring a first image of the sample;
   acquiring the first image of the sample;
   applying amplitude modulated RF irradiation with a magnetic field gradient which, together, mimic the effects of constant RF radiation unrelated to blood flow;
   acquiring a second image of the sample;
   generating a difference signal based on the first image and the second image that represents a blood flow image of blood flowing into the sample; and
   determining a duration of the transit delay period so as to ensure that blood having perturbed arterial spins remains in a blood vessel of the sample, thus causing the blood flow image to be representative of large vessel blood flow.

3. A method for measuring blood flow, comprising the steps of:
   perturbing arterial spins of blood flowing into a sample by applying a constant RF irradiation together with a magnetic field gradient;
   acquiring a first image of the sample;
   applying amplitude modulated RF irradiation with a magnetic field gradient which, together, mimic the effects of constant RF radiation unrelated to blood flow;
   acquiring a second image of the sample, wherein the step of acquiring the first image and the step of acquiring the second image each comprises detecting an analog magnetic resonance signal reflected off of the sample;

generating a difference signal based on the first image and the second image that represents a blood flow image of blood flowing into the sample;

digitizing the analog magnetic resonance signal to form digital magnetic resonance signals; and measuring the blood flow into the sample based on the digital magnetic resonance signals.

4. A method for generating a signal representative of a blood flow image, comprising the steps of:

perturbing arterial spins of blood flowing into a sample by applying a constant RF irradiation together with a magnetic field gradient;

acquiring a first image of the sample;

applying amplitude modulated RF irradiation with a magnetic field gradient which, together, mimic the effects of constant RF radiation unrelated to blood flow;

acquiring a second image of the sample; and generating a difference signal based on the first image and the second image that represents a blood flow image of blood flowing into the sample.

\* \* \* \* \*

UNITED STATES PATENT AND TRADEMARK OFFICE
CERTIFICATE OF CORRECTION

PATENT NO. : 7,369,888 B2  Page 1 of 1
APPLICATION NO. : 11/198581
DATED : May 6, 2008
INVENTOR(S) : David C. Alsop It is certified that error appears in the above-identified patent and that said Letters Patent is hereby corrected as shown below:

Column 4,
Line 33, delete "image.slice" and insert -- image slice --.
Line 51, after "resonance" delete ".".

Column 5,
Line 46, delete "In.the" and insert -- In the --.

Column 6,
Line 31, after "generated." there should be a new paragraph starting with "During evaluation....".

Column 8,
Line 12, after "perpendicular" delete ".".

Signed and Sealed this

Eighth Day of September, 2009

David J. Kappos
*Director of the United States Patent and Trademark Office*